United States Patent [19]

Kunstmann et al.

[11] 4,118,494
[45] * Oct. 3, 1978

[54] SUBSTITUTED 3,4-DIHYDRO-2H-ISOQUINOLIN-1-THIONES

[75] Inventors: Rudolf Kunstmann, Breckenheim; Joachim Kaiser, Bad Soden, both of Fed. Rep. of Germany

[73] Assignee: Hoechst Aktiengesellschaft, Frankfurt am Main, Fed. Rep. of Germany

[ * ] Notice: The portion of the term of this patent subsequent to Mar. 29, 1994, has been disclaimed.

[21] Appl. No.: 754,168

[22] Filed: Dec. 27, 1976

Related U.S. Application Data

[63] Continuation of Ser. No. 649,498, Jan. 15, 1976, abandoned, which is a continuation-in-part of Ser. No. 604,011, Aug. 12, 1975, abandoned.

[30] Foreign Application Priority Data

Aug. 14, 1974 [DE] Fed. Rep. of Germany ....... 2438966

[51] Int. Cl.² .................... A61K 31/47; C07D 217/24
[52] U.S. Cl. ................ 424/258; 260/287 K; 260/288 D; 260/288 CE; 260/293.51; 260/293.88; 260/326.8; 260/453 AR; 562/441; 562/442; 562/451
[58] Field of Search .................. 260/288 D, 288 CE; 424/258

[56] References Cited

U.S. PATENT DOCUMENTS

| | | | |
|---|---|---|---|
| 2,759,936 | 8/1956 | Speeter | 260/288 D |
| 3,457,266 | 7/1969 | Gibas et al. | 260/288 D |
| 3,462,438 | 8/1969 | Loev | 260/289 K |
| 3,480,634 | 11/1969 | Finkelstein | 260/288 D |
| 3,980,655 | 9/1976 | Kunstmann et al. | 260/288 D |
| 4,014,884 | 3/1977 | Kunstmann et al. | 260/288 D |

*Primary Examiner*—Donald G. Daus
*Assistant Examiner*—David E. Wheeler
*Attorney, Agent, or Firm*—Curtis, Morris & Safford

[57] ABSTRACT

The invention relates to 3,4-Dihydro-2H-isoquinoline-1-ones and a process for preparing them.

The compounds have an antiarrhythmic activity and are suitable for treating disturbance of the cardiac rhythm.

5 Claims, No Drawings

SUBSTITUTED 3,4-DIHYDRO-2H-ISOQUINOLIN-1-THIONES

This is a continuation of application Ser. No. 649,498 filed Jan. 15, 1976 and now abandoned, which is in turn a continuation-in-part of application Ser. No. 604,011 filed Aug. 12, 1975 and also now abandoned.

3,4-Dihydro-2H-isoquinoline-1-ones having a neutral substituent in 3,4,5- or 6 position are already known. In U.S. Pat. No. 2,647,902 and Britain patent specification No. 721,286 such compounds acting as a local anesthetic are described. In German Offenlegungsschrift No. 2,143,744 analogous compounds having a hypolipidemic activity are claimed. A synthesis of 3,4-dihydro-2H-isoquinoline-1-ones is described in J. Chem. Soc. (1956), 2557, and some derivatives are mentioned in J. Heteroc. Chem. 7, 615 (1970).

Now 3,4-dihydro-2H-isoquinoline-1-ones basically substituted in 4-position acting on coranary circulation have been found. Therefore, the invention relates to 3,4-dihydro-isoquinolines of the formula I

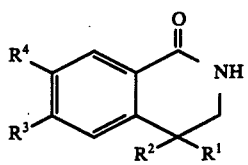

wherein $R_1$ is hydrogen, a saturated or unsaturated, straight-chained or branched alkyl radical having 1 to 6 carbon atoms or the phenyl radical, $R_2$ is a dialkylaminoalkyl radical of the formula

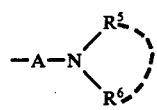

wherein A is a straight-chained or branched low molecular alkylene group and $R^5$ and $R^6$ are identical or different and are straight-chained or branched, low molecular alkyl radicals and may form together with the nitrogen atom a 5-, 6- or 7-membered ring, wherein one of the hydrocarbons is substituted by a hetero atom preferably the oxygen, sulfur or nitrogen atom optionally substituted with hydrogen, $C_1$-$C_4$-alkyl or the phenyl radical, $R^3$ and $R^4$ are identical or different and represent hydrogen or a lower alkoxy group having 1 to 4 carbon atoms, as well as the physiologically tolerable salts thereof.

Preferred substituents are for $R^1$ the methyl, ethyl or phenyl radical, for $R^2$ a dialkylaminoalkyl radical of the formula

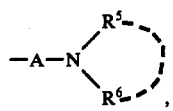

wherein A is a straight-chained or branched alkylene group having 2 or 3 carbon atoms and $R^5$ and $R^6$ represent identical alkyl radicals having 1 to 4 carbon atoms or $R^5$ and $R^6$ represent together with the nitrogen atom a 5- or 6-membered ring or the morpholine radical, and for $R^3$ and $R^4$ hydrogen or the methoxy group.

The invention further relates to processes for preparing the compounds of the formula I as well as pharmaceutical compositions containing these compounds.

The process for preparing the compounds of the invention comprises (a) cyclizing a compound of the formula IIa or IIb

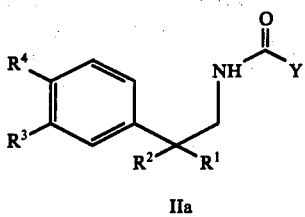

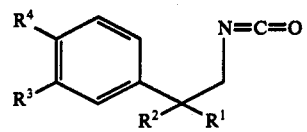

wherein $R^1$ to $R^4$ have the above meaning and Y is an optionally substituted amino group, O-alkyl or S-alkyl or S-phenyl radical, or (b) replacing the sulfur atom by an oxygen atom in a usual manner in a compound of the formula III

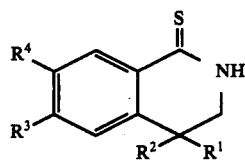

wherein $R^1$ to $R^4$ have the meaning mentioned in formula I (c) carrying through a Beckmann re-arrangement with an oxime of the formula IV

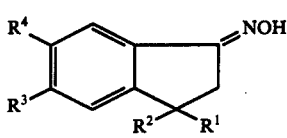

wherein $R^1$ to $R^4$ have the meaning mentioned in formula I, or the O-derivatives thereof (d) reducing selectively an imide of the formula V

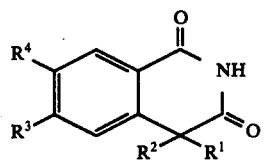

wherein $R^1$ to $R^4$ have the meaning mentioned in formula I, or (e) cyclizing an amino acid derivative of the formula VI

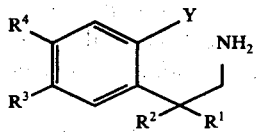

wherein $R^1$ to $R^4$ have the meaning mentioned in formula I, and Y is a carboxy group or the derivative thereof, or a hydroxy carboxylic acid amide of the formula VII

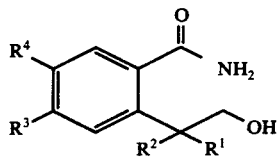

wherein $R^1$ to $R^4$ have the meaning mentioned in formula I, or (f) hydrogenating a compound of the formula VIII

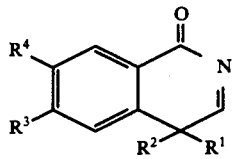

wherein $R^1$ to $R^4$ have the meaning mentioned in formula I, or (g) cyclizing a N-hydroxyalkyl-substituted benzoic acid amide of the formula IX

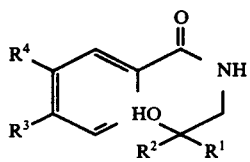

wherein $R^1$ to $R^4$ have the meaning indicated in formula I, or (h) replacing the oxygen of the lactone ring by nitrogen in a compound of the formula X

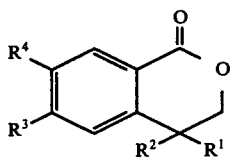

wherein $R^1$ to $R^4$ have the meaning given in formula I, or (j) subsequently introducing the substituents $R^1$ and/or $R^2$ by alkylation into a compound of the formula I, wherein $R^1$ and/or $R^2$ represent hydrogen and $R^3$ and $R^4$ have the mentioned meaning, or (k) reacting a compound of the formula XI

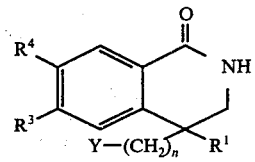

wherein $R^1$, $R^3$ and $R^4$ have the meaning given in formula I and wherein n is an integer of 1 to 4 and Y is a substituent which may be replaced by a secundary amine, with a secondary amine or (l) subsequently substituting the amino group in a compound of the formula XII

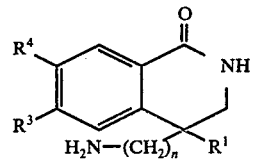

wherein $R^1$, $R^3$ and $R^4$ have the meaning given in formula I and wherein n is an integer of from 1 to 4, or (m) cyclizing a compound of the formula XIII

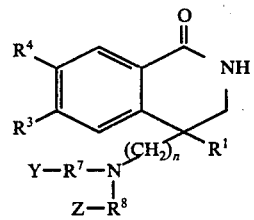

wherein $R^1$, $R^3$ and $R^4$ have the meaning mentioned in formula I, n is an integer of from 1 to 4, $R^7$ and $R^8$ are a low-molecular alkyl radical and Y and Z are the hydroxyl, mercapto or amino group, or (n) cyclizing with a primary amine or by treatment with water a compound of the formula XIII, wherein $R^1$, $R^3$, $R^4$, $R^7$, $R^8$ and n have the meaning mentioned and Y and Z are a radical which may be substituted by a primary amine or water.

The preparation of the starting materials of the formula IIa and IIb for the method (a) is effected via an amine of the formula XIV

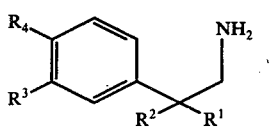

which may be prepared by catalytic hydrogenation of the corresponding nitrile of the formula XV

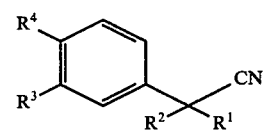

This nitrile may be obtained by alkylation of the corresponding benzyl cyanide of the formula XVI

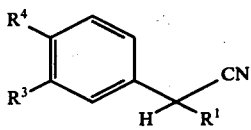

XVI with an alkyl halide in the presence of sodium amide in an inert solvent, expediently according to the method described in Liebigs Annalen 561, 52 (1949) (method A).

The compounds of the formula XVI may also be obtained according to this method from the corresponding benzyl cyanides ($R^1 = H$).

The preparation of diphenyl-acetonitriles ($R^1$ = phenyl) which have substituents in one of the phenyl rings, is carried out according to a process of T. Kametani et al., J. Org. Chem. 36, 327 (1971). An ortho-halogenalkoxy-benzene is reacted with $NaNH_2$ in an inert solvent such as benzene, toluene or THF to obtain the corresponding dehydrobenzene, which adds benzyl cyanide in situ and yields the desired substituted derivative (method B).

The nitrile of the formula XV thus prepared is hydrogenated to an amine of the formula XIV in ethanol or methanol saturated with ammonia with Raney-Nickel as a catalyst, at a pressure of 70–120 atmospheres gauge and 100°–125° C. during 8–36 hours. The operation is expediently carried out according to Org. Synth. 23, 71 (1943). The amine obtained of the formula XIV is converted according to usual methods into a derivative of the isocyanic acid IIa or IIb capable of ring closure. Isocyanates are prepared for example from the amines of the formula XIV with phosgene in an inert solvent such as benzene, toluene, acetic acid or chlorobenzene. It is expedient to follow the prescription of Org. Synth. Coll. Vol. II, 453 (1943) or in Liebigs Ann. Chem. 562, 105, 106 (1949).

Carbamic acid esters (IIa, Y = OR) are prepared in the simplest way according to a modified method, described in Org. Synth. Coll. Vol. II, 278 (1943). In the presence of a base such as $Na_2CO_3$ or NaOH the amine is reacted with a chloroformic acid ester in an inert solvent such as toluene, benzene, chlorobenzene, ethyl acetate or a chlorinated hydrocarbon such as $CCl_4$ or trichloroethylene at an elevated temperature. Another method consists in heating an isocyanate of the formula IIb with the calculated amount of alcohol with or without addition of an inert solvent as for example benzene or ethyl acetate (cf. J. Am. Chem. Soc. 62, 218 (1940)).

To prepare the ureas (IIa, Y = $NH_2$) for example the prescriptions in J. Am. Chem. Soc. 51, 1797 (1929) are used. The amine of the formula XIV is reacted with nitro-urea in water or a water/alcohol mixture at room temperature or while heating gently. Alkylated ureas (formula IIa, Y = NHR or NRR', wherein R and R' are identical or different and represent alkyl radicals having 1 to 4 carbon atoms) are prepared from the isocyanates (IIb) with a primary or secondary amine in an inert solvent such as benzene, toluene, chlorobenzene or an aliphatic chlorinated hydrocarbon according to R. 51, 432 (1932).

Thiocarbamic acid esters (formula IIa, Y = SR, wherein R is an alkyl radical having 1 to 4 carbon atoms) are prepared according to the method described in Liebigs Annalen 562, 210 (1949). At elevated temperature the isocyanate (IIb) is reacted with a mercaptan in the autoclave.

Preferred compounds of the formula IIa are carbamic acid esters (Y = O-alkyl having 1 to 4 carbon atoms or Y = O-phenyl) as well as urea derivatives with Y = N-alkyl (1–4 carbon atoms) or N-phenyl.

Method (a)

The reaction according to method (a) is effected according to known methods. The compounds of the formula IIa or IIb are reacted in the presence of a catalyst with or without solvent. As catalysts there are preferably used anhydrous or practically anhydrous acid catalysts, preferably polyphosphonic acid, phosphorous oxychloride, concentrated sulfuric acid or Lewis acids, as for example $AlCl_3$. As solvents—as far as they are used for the reaction—there are considered inert anhydrous organic solvents, especially chlorinated hydrocarbons, as for example $CCl_4$ or trichloroethylene, furthermore $CS_2$ or aromatic hydrocarbons such as benzene, toluene or xylene. The temperatures used depend on the reactants used and vary between −15° C. and +150° C.

Method (b)

The starting compounds of the formula III for the method (b) are also prepared according to known methods. As starting materials are used compounds of the formulae IIa and IIb, which contain a sulfur atom instead of the oxygen. The preparation of these compounds is effected in analogous manner from the amines of the formula XIV. The preparation of the isothiocyanates is expediently carried out according to J. Am. Chem. Soc. 81, (1959) page 4328.

According to this reference an amine of the formula XIV is converted with $CS_2$ and a base such as for example triethyl amine in the presence of chloroformic acid esters into a dithiocarbamic acid ester which provides the corresponding isothiocyanate with an excess of the base. Another method consists in reacting the amine of the formula XIV or the hydrochloride thereof with thiophosgene in the presence of a base such as $Na_2CO_3$ or $CaCO_3$ in an aqueous medium (cf. Houben-Weyl "Methoden der organischen Chemie", volume IX, 875 (1955).

For the preparation of O-alkyl-thiocarbamic acid esters, as starting materials are expediently used the isothiocyanates which are reacted with an alcohol or an alcoholate, dissolved in the corresponding alcohol, to obtain the compounds desired at temperatures between 20° and 80° without additional solvent.

These methods are described for example in J. Am. Chem. Soc. 77, 581 (1955) as well as 65, 900, (1943).

The dithio-carbamic acid esters may also be obtained from the isothiocyanates by reaction with mercaptans. The mercaptan is dissolved in a 20–30% sodium hydroxide solution, the isothiocyanate is added dropwise and then the mixture is acidified (Chem. Abstr. (1910), 910).

For the preparation of the thio-ureas, the starting components are either the amine of the formula XIV which is reacted with ammonium rhodanide in water in the presence of a mineral acid (for example HCl) at elevated temperature to obtain thiourea (cf. Arzneimittel-Forschung 2, 125 (1952)), whereby the operation may also be carried out in an inert solvent, for example chlorobenzene saturated with HCl, or the isothicyanate is reacted at room temperature in an aqueous alcoholic ammonia solution to obtain the thio-urea (cf. Chem. Ber. 80, 275 (1947)).

The preparation of the N-mono-substituted thio-ureas is carried out according to J. Am. Chem. Soc. 51, 1909 (1929) as follows: the amine of the formula XIV is refluxed with an isothiocyanate without solvent or dissolved in alcohol. For N,N-disubstituted thio-ureas, the isothiocyanate (IIb) is reacted with a secondary amine at 0° C. or under reflux in an inert solvent such as benzene, toluene, chlorobenzene or acetic acid (cf. Chem. Ber. 28, 2935 (1895).

The conversion of a compound of the formula III into a compound of the formula I according to method (b) is carried out according to known methods. Expediently a compound of the formula III is reacted with an alkyl halide which may be basically substituted, whereby the thion of the formula III reacts formally in its tautomeric imino form. The operation is expediently carried out in the presence of a base, as for example potassium carbonate, in an inert solvent such as benzene, toluene, xylene, acetone or methylethyl ketone at elevated temperature whereby a S-alkyl compound is obtained which is desulfurized with mineral acid, as for example hydrochloric acid at elevated temperature. A compound of the formula III may also be converted directly into a compound of the formula I with mineral acid or with alkali. Furthermore, it is possible to desulfurize the compounds of the formula III with a peroxide as for example $Na_2O_2$ in an alkaline medium to obtain the desired compounds of the formula I. Moreover, the 3,4-dihydro-2H-isoquinoline-1-thiones of the formula III may also be oxidized with $SeO_2$ in alcohol at elevated temperature to obtain the oxygen compounds of the formula I. It is also possible to convert the sulfur compounds into the corresponding oxygen compounds with potassium hexacyano-ferrate-(III) in ethanol or with silver nitrate in aqueous alcohol (cf. R. Boudet Bl./5/, 18, 846 (1951).

Method (c)

The oximes of the formula IV required for the method (c) are obtained for example according to J. Chem. Soc. (C), page 2245 (1970).

The starting compound is a suitably substituted indan-1-one of the formula XVII

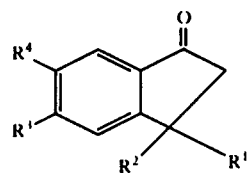

XVII wherein $R^1$ to $R^4$ has the meaning indicated in formula 1 and this compound is reacted in usual way to an oxime of the formula IV.

As O-derivatives of the oxime there are especially considered the methyl sulfonic acid ester and the p-toluene sulfonic acid ester, which are prepared in the usual way. The Beckmann-rearrangement according to method (c) is expediently carried out under acidic conditions or in the case of substituted oximes also under alkaline conditions.

Method (d)

The preparation of the compounds V serving as starting materials for the process (d) is effected according to known methods. The procedure is expediently the following one: At first, by introducing a protective group with a suitable reagent such as chloroformic acid ester under alkylating conditions, for example with alcoholate in alcohol or sodium amide in inert solvents such as for example benzene, the imide group of the homophthalic acid imide is protected. Then the substitutents $R^1$ and $R^2$ are introduced into the compound thus obtained of the formula XVIII

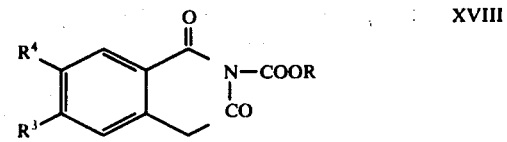

XVIII by stepwise alkylation for example with sodium amide in inert solvents such as benzene or toluene; it is not important if substitution is carried out at first with $R^1$ or $R^2$. Subsequent saponification and decarboxylation, for example by treating with acids or bases in water, alcohols or aqueous alcohols leads to the compunds of the formula V.

The reduction of a compound of formula V yielding a compound of formula I is carried out according to known methods. It is advantageous to reduce a compound of the formula V to a compound of the formula I in an aqueous acetic acid medium or in anhydrous acetic acid, if desired with addition of a mineral acid catalyst, for example hydrochloric acid, in the presence of zinc dust. The operation is preferably carried out at temperatures between room temperature and the boiling point of the solvent. Suitable complex hydrides may also be used for reduction. Operation is carried out for example with sodium borohydride in solvents as for example methanol, dioxane or dimethoxy-ethane or in mixtures of the solvents mentioned, whereby mixtures with water may be used, at temperatures between room temperature and the boiling point of the solvent.

Method (e)

Amino acid derivatives of the formula VI and hydroxy-carboxylic acid derivatives of the formula VII which may be prepared according to one of the usual methods may be cyclized with or without acid catalysts such as sulfuric acid or phosphoric acid, or with or without agents splitting off hydrogen, as for example acetic acid anhydride or thionyl chloride, with or without solvents such as glacial acetic acid, alcohol or ether at temperatures between room temperature and the boiling point of the solvent.

Method (f)

The compounds of the formula VIII mentioned under (f) are prepared according to one of the usual methods, whereby it is expedient to choose as starting component an isoquinoline of the formula XIX which carries in 4-position one of the two radicals $R^1$ or $R^2$.

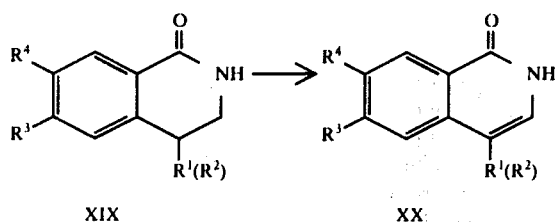

XIX    XX

Dehydrogenation (XIX-XX) is carried out according to known methods. There is considered above all the dehydrogenation of a compound of the formula XIX in the presence of a metal catalyst as for example Raney-Nickel or palladium at elevated temperature. The operation is preferably carried out using a melt without a solvent, but the reaction may also be carried out in a solvent inert under these conditions, as for example diphenyl ether or dimethoxy-ethylene-glycol. There may also be used a protective gas or oxygen or an inert gas, for example nitrogen or carbon dioxide, may be introduced into the reaction mixture until the reaction is complete (J. Chem. Soc. 1146 (1937)). Further dehydrogenationg agents are quinones of the chloroanile type or 2,3-dichloro-5,6-dicyano-1,4-benzoquinone. Dehydrogenations of this type are carried out in inert solvents, as for example ethers, such as dioxane or dimethoxy-ethane, or a chlorinated hydrocarbon, as for example chlorobenzene or trichloro-ethylene, at room temperature or a temperature up to the boiling point of the solvent (Advances in Organic Chemistry, Methods and Results 2, 329 (1960)). The compounds thus prepared of the formula XX are enamines into which under alkylating conditions the radical $R^2$ (or $R^1$) is introduced in the usual way.

The compounds thus obtained of the formula VIII which may also be used as crude product are hydrogenated according to method (f) preferably catalytically in the presence of metal catalysts, preferably Raney-Nickel or palladium on charcoal, in suitable solvents, preferably in alcohol or ether. Suitable complex hydrides may also be used for reduction. The operation is expediently carried out with sodium borohydride in solvents, as for example methanol, dioxane or dimethoxy-ethane at temperatures between room temperature and the boiling point of the solvent.

Method (g)

The reaction according to process (g) works well under conditions indicated for the process (a).

Method (h)

Chromanones of the formula X, which may be synthetized from the corresponding open-chained hydroxybenzoic acids, are reacted to form compounds of the formula I according to method (h) with ammonia or the salts thereof with or without solvent such as alcohol, if desired at pressures up to 150 atmospheres, at temperatures between 50° C. and 200° C. The conditions of U.S. Pat. No. 3,480,634 may also be applied.

Method (j)

The subsequent introduction of the substituents $R^1$ and/or $R^2$ into the isoquinoline structure of the formula XXI according to process (i)

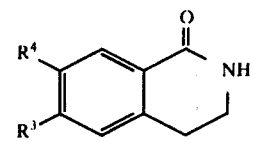

XXI is effected according to known methods; it is expedient first to protect the amide group with a suitable reagent, as for example chloroformic acid ester, under alkylating conditions, for example with alcoholate in alcohol or sodium amide in inert solvents such as benzene. Into the compound thus obtained of the formula XXII

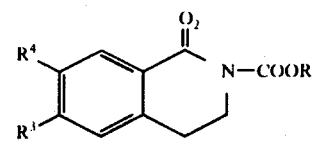

XXII the substituents $R^1$ and/or $R^2$ are introduced by stepwise alkylation, preferably with sodium amide in inert solvents, for example benzene or toluene, whereby it is not important if substitution is carried out first with $R^1$ or $R^2$. Subsequent saponification and decarboxylation, preferably by treatment with acids or bases in water, alcohols or aqueous alcohols lead to the compounds of the formula I.

The compounds XI, XII, XIII for the processes (k), (l), (m) and (n) may be synthetized according to known methods, or one of the ways of synthesis mentioned above under (a) to (j) is used.

Method (k)

The reaction according to process (k), whereby Y in XI preferably is a halogen atom such as Cl or J, or another radical which may be substituted by a secondary amine, for example the p-toluene sulfonic acid or methane sulfonic acid radical, is effected in the presence of an excess of the secondary amine to be used, or if the secondary amine is added in a stoichiometric amount, with addition of a base preferably such as sodium hydroxide solution, aqueous sodium carbonate solution, triethyl amine or alcoholate, in suitable solvents, as for example water, alcohols, such as methanol or butanol, ethers such as diethyl ether or dimethoxy ethylene, aromatic or aliphatic, optionally halogenated hydrocarbons such as cyclohexane, chloroform, toluene or chlorobenzene, polar solvents such as dimethyl sulfoxide or dimethylformamide or mixtures of the solvents mentioned, at a temperature between room temperature and the boiling point of the solvent used.

Method (l)

The alkylation of a compound of the formula XII according to the process (l) works according to known methods, whereby alkylation is preferably carried out with an alkyl ester of an organic or mineral acid such as dimethyl or diethyl sulfate or a benzenesulfonic acid alkyl ester (for example according to Org. Synth. 44, 72 (1964), Pharm. Chem. J. 193, (1969)), or a compound of the formula XII is subjected to a reaction with a corresponding alkyl compound, whereby the conditions indicated for the process (k) are applied. The two alkyl radicals may also be introduced successively. In this respect, there is considered the reaction of the amine with an aldehyde or ketone to obtain the Schiff base, subsequent alkylation of the Schiff base and hydrogenation of the imonium salt. The prescription indicated in Chem. Inform. 16–258 (1973) is advantageously observed.

Method (m)

The compounds of the formula XIII are cyclized according to known methods. Cyclization may be carried out in the presence of a catalyst, but also without catalyst, either in an inert solvent or without a solvent. It is expedient that a compound of the formula XIII is maintained in an inert solvent in the presence of an acid catalyst, preferably boron trifluoride etherate or p-toluene-sulfonic acid, until the reaction is complete, at temperatures between 0° C. and the boiling point of the solvent used. As solvents there are considered preferably ethers such as tetrahydrofurane or dimethoxyethane or, if desired, chlorinated aliphatic or aromatic hydrocarbons such as cyclohexane, methylene chloride, chlorobenzene or toluene. If Y and/or Z represent the hydroxy group, the reaction formed may preferably be separated with the aid of a water separator.

Method (n)

The reactions according to process (n) are preferably carried out at conditions indicated for the process (k). Y and Z represent in this case a radical which may be substituted by a secondary amine or water and represent for example chlorine or iodine or the p-toluene-sulfonic acid or methane sulfonic acid radical.

Besides the compounds mentioned in the Examples the following compounds of the invention may be preferably used:

4-(2-Diethylaminoethyl-)-3,4-dihydro-2H-isoquinolin-1-one
4-(2-Dimethylaminopropyl)-3,4-dihydro-2H-isoquinolin-1-one
4-(2-Diisoproyplaminoethyl)-3,4-dihydro-2H-isoquinolin-1-one
4-(2-Dimethylaminoethyl)-3,4-dihydro-2H-isoquinolin-1-one
4-(2-Dibutylaminoethyl)-3,4-dihydro-2H-isoquinolin-1-one
4-[2(1-Pyrrolidinyl)ethyl]-3,4-dihydro-2H-isoquinolin-1-one
4-[2-(1-Piperidinyl)-ethyl]-3,4-dihydro-2H-isoquinolin-1-one
4-Methyl-4-(2-dimethylaminoethyl)-3,4-dihydro-2-H-isoquinolin-1-one
4-Methyl-4-(2-diisopropylaminoethyl)-3,4-dihydro-2H-isoquinolin-1-one
4-Methyl-4-[2-(1-pyrrolidinyl)ethyl]-3,4-dihydro-2H-isoquinolin-1-one
4-Methyl-4-[2-(1-piperidinyl)ethyl]-3,4-dihydro-2H-isoquinolin-1-one
4-Ethyl-4-(2-dimethylaminoethyl)-3,4-dihydro-2H-isoquinolin-1-one
4-Ethyl-4-(2-diisopropylaminoethyl)-3,4-dihydro-2H-isoquinolin-1-one
4-Ethyl-4-[2-(1-pyrrolidinyl)ethyl]-3,4-dihydro-2H-isoquinolin-1-one
4-Ethyl-4-[2-(1-piperidinyl)ethyl]-3,4-dihydro-2H-isoquinolin-1-one
4-Propyl-4-(2-dimethylaminoethyl)-3,4-dihydro-2H-isoquinolin-1-one
4-Propyl-4-(2-diethylaminoethyl)-3,4-dihydro-isoquinolin-1-one
4-Propyl-4-(2-diisopropylaminoethyl)-3,4-dihydro-2H-isoquinolin-1-one
4-Propyl-4-[2-(1-pyrrolidinyl)ethyl]-3,4-dihydro-2H-isoquinolin-1-one
4-Propyl-4-[2-(1-piperidinyl)ethyl]-3,4-dihydro-2H-isoquinolin-1-one
6-Methoxy-4-(2-diethylaminoethyl)-3,4-dihydro-2H-isoquinolin-1-one
6-Methoxy-4-(2-dimethylaminopropyl)-3,4-dihydro-2H-isoquinolin-1-one
6-Methoxy-4-(2-diisopropylaminoethyl)-3,4-dihydro-2H-isoquinolin-1-one
6-Methoxy-4-(2-dimethylaminoethyl)-3,4-dihydro-isoquinolin-1-one
6-Methoxy-4-(2-dibutylaminoethyl)-3,4-dihydro-isoquinolin-1-one
6-Methoxy-4-[2-(1-pyrrolidinyl)ethyl]-3,4-dihydro-isoquinolin-1-one
6-Methoxy-4-[2-(1-piperidinyl)-ethyl]-3,4-dihydro-isoquinolin-1-one
6-Methoxy-4-methyl-4-(2-dimethylaminoethyl)-3,4-dihydro-2H-isoquinolin-1-one
6-Methoxy-4-methyl-4-(2-diethylaminoethyl)-3,4-dihydro-2H-isoquinolin-1-one
6-Methoxy-4-methyl-4-(2-diisopropylaminoethyl)-3,4-dihydro-2H-isoquinolin-1-one
6-Methoxy-4-methyl-4-[2-(1-pyrrolidinyl)-ethyl]-3,4-dihydro-2H-isoquinolin-1-one
6-Methoxy-4-methyl-4-[2-(1-piperidinyl)ethyl]-3,4-dihydro-2H-isoquinolin-1-one
6-Methoxy-4-ethyl-4-(2-dimethylaminoethyl)-3,4-dihydro-2H-isoquinolin-1-one
6-Methoxy-4-ethyl-4-(2-diethylaminoethyl)-3,4-dihydro-2H-isoquinolin-1-one
6-Methoxy-4-ethyl-4-(2-diisopropylaminoethyl)-3,4-dihydro-2H-isoquinolin-1-one
6-Methoxy-4-ethyl-4-[2-(1-pyrrolidinyl)ethyl]-3,4-dihydro-2H-isoquinolin-1-one
6-Methoxy-4-ethyl-4-[2-(1-piperidinyl)ethyl]-3,4-dihydro-2H-isoquinolin-1-one
6-Methoxy-4-propyl-4-(2-dimethylaminoethyl)-3,4-dihydro-2H-isoquinolin-1-one
6-Methoxy-4-propyl-4-(2-diisopropylaminoethyl)-3,4-dihydro-2H-isoquinolin-1-one
6-Methoxy-4-propyl-4-[2-(1-pyrrolidinyl)ethyl]-3,4-dihydro-2H-isoquinolin-1-one
6-Methoxy-4-propyl-4-[2-(1-piperidinyl)-ethyl]-3,4-dihydro-2H-isoquinolin-1-one
6,7-Dimethoxy-4-(2-dimethylaminopropyl)-3,4-dihydro-2H-isoquinolin-1-one
6,7-Dimethoxy-4-(2-diisopropylaminoethyl)-3,4-dihydro-2H-isoquinolin-1-one
6,7-Dimethoxy-4-(2-dimethylaminoethyl)-3,4-dihydro-2H-isoquinolin-1-one
6,7-Dimethoxy-4-(2-dibutylaminoethyl)-3,4-dihydro-2H-isoquinolin-1-one
6,7-Dimethoxy-4-[2-(1-pyrrolidinyl)-ethyl]-3,4-dihydro-2H-isoquinolin-1-one
6,7-Dimethoxy-4-[2-(1-piperidinyl)-ethyl]-3,4-dihydro-2H-isoquinolin-1-one
6,7-Dimethoxy-4-methyl-4-(2-dimethylaminoethyl)-3,4-dihydro-2H-isoquinolin-1-one
6,7-Dimethoxy-4-methyl-4-(2-diethylaminoethyl)-3,4-dihydro-2H-isoquinolin-1-one
6,7-Dimethoxy-4-methyl-4-(2-diisopropylaminoethyl)-3,4-dihydro-2H-isoquinolin-1-one
6,7-Dimethoxy-4-methyl-4-(1-pyrrolidinyl)-ethyl-3,4-dihydro-2H-isoquinolin-1-one 6,7-Dimethoxy-4-methyl-4-[2-(1-piperidinyl)-ethyl]-3,4-dihydro-2H-isoquinolin-1-one
6,7-Dimethoxy-4-ethyl-4-(2-dimethylaminoethyl)-3,4-dihydro-2H-isoquinolin-1-one
6,7-Dimethoxy-4-ethyl-4-(2-diethylaminoethyl)-3,4-dihydro-2H-isoquinolin-1-one
6,7-Dimethoxy-4-ethyl-4-(2-diisopropylaminoethyl)-3,4-dihydro-2H-isoquinoline
6,7-Dimethoxy-4-ethyl-4-[2-(1-pyrrolidinyl)-ethyl]-3,4-dihydro-2H-isoquinolin-1-one
6,7-Dimethoxy-4-ethyl-4-[2-(1-piperidinyl)-ethyl]-3,4-dihydro-2H-isoquinolin-1-one
6,7-Dimethoxy-4-propyl-4-(2-dimethylaminoethyl)-3,4-dihydro-2H-isoquinolin-1-one
6,7-Dimethoxy-4-propyl-4-(2-diethylaminoethyl)-3,4-dihydro-2H-isoquinolin-1-one
6,7-Dimethoxy-4-propyl-4-(2-diisopropylaminoethyl)-3,4-dihydro-2H-isoquinolin-1-one
6,7-Dimethoxy-4-propyl-4-[2-(1-pyrrolidinyl)-ethyl]-3,4-dihydro-2H-isoquinolin-1-one
6,7-Dimethoxy-4-propyl-4-[2-(1-piperidinyl)-ethyl]-3,4-dihydro-2H-isoquinolin-1-one
6-Methoxy-4-phenyl-4-(2-dimethylaminoethyl)-3,4-dihydro-2H-isoquinolin-1-one
6-Methoxy-4-phenyl-4-(2-diethylaminoethyl-3,4-dihydro-2H-isoquinolin-1-one
6-Methoxy-4-phenyl-4-[2-(1-pyrrolidinyl)-ethyl]-3,4-dihydro-2H-isoquinolin-1-one
6-Methoxy-4-phenyl-4-[2-(1-piperidinyl)-ethyl]-3,4-dihydro-2H-isoquinolin-1-one
6-Methoxy-4-phenyl-4-[2-(1-morpholinyl)-ethyl]-3,4-dihydro-2H-isoquinolin-1-one
6,7-Dimethoxy-4-phenyl-4-(2-dimethylaminoethyl)-3,4-dihydro-2H-isoquinolin-1-one
6,7-Dimethoxy-4-phenyl-4-(2-diethylaminoethyl)-3,4-dihydro-2H-isoquinolin-1-one
6,7-Dimethoxy-4-phenyl-4-(2-diisopropylaminoethyl)-3,4-dihydro-2H-isoquinolin-1-one
6,7-Dimethoxy-4-phenyl-4-[2-(1-pyrrolidinyl)-ethyl]-3,4-dihydro-2H-isoquinolin-1-one
6,7-Dimethoxy-4-phenyl-4-[2-(1-piperidinyl)-ethyl]-3,4-dihydro-2H-isoquinolin-1-one
6,7-Dimethoxy-4-phenyl-4-[2-(1-morpholinyl)-ethyl]-3,4-dihydro-2H-isoquinolin-1-one The compounds of the invention have valuable therapeutical properties. Thus, besides other pharmacological properties, they have an action on coronary circulation which shows itself particularly in an antiarrhythmic activity. These compounds are, thus, suitable for the treatment of disturbances of the cardiac rhythm. The antiarrhythmic activity was detected on isolated papillary muscles of guinea pigs and on dogs, to which strophanthin has been administered.

The novel compounds of the invention may be used either individually or mixed with pharmacologically compatible carriers. For oral administration the active compounds are mixed with the suitable substances and brought by usual methods into suitable administration forms such as tablets, gelatin capsules, aqueous, alcoholic or oily suspensions or aqueous alcoholic or oily solutions. As inert carriers there may be used for example magnesium carbonate, lactose or cornstarch with addition of other substances, as for example magnesium stearate. The preparation may be carried out as dry or moist granules. As oily carriers or solvents there are especially considered vegetable and animal oils, as for example sunflower oil or cod-liver oil.

A special administration form is the intravenous administration. For this purpose the active compounds or the physiologically tolerable salts thereof are brought into solution with the usual substances. Such physiologically tolerable salts are formed for example with the following acids: hydrochloric acid, hydrobromic acid or hydriodic acid, phosphoric acid, sulfuric acid, methylsulfuric acid, amidosulfonic acid, nitric acid, formic acid, acetic acid, propionic acid, succinic acid, tartric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-amino-salicylic acid, hydroxyethane-sulfonic acid, benzene-sulfonic acid or synthetic resins containing acid groups, for example those having the effect of ion exchangers.

As solvents of the corresponding physiologically tolerable salts of the active compounds for intravenous administration there may be mentioned for example: water, physiological sodium chloride solution or alcohols such as for example ethanol, propane-diol or glycerol, furthermore sugar solutions as for example glucose or mannitol solutions or a mixture of the different solvents mentioned.

The unit dosage for a human being is for intravenous administration 0.3 to 10 mg/kg, preferably 0.5 to 6 mg/kg, and for oral administration 1 to 30 mg/kg, preferably 2 mg to 20 mg/kg.

As daily dosage unit there may be considered for intravenous administration 0.3 mg to 500 mg/kg, preferably 1 mg to 50 mg/kg, for oral administration 2 mg to 500 mg/kg, preferably 10 mg to 150 mg/kg.

The following Examples illustrate the invention.

EXAMPLE 1

4-(3-Dimethylaminopropyl)-4-phenyl-3,4-dihydro-2H-isoquinolin-1one (a) 2,2-Diphenyl-5-dimethylaminopentyl-isothiocyanate To a stirred solution of (0.35 mol) of 2,2-diphenyl-5-dimethylaminopentylaminohydrochloride in 140 ml of dry chloroform, 107 ml (0.77 mol) of triethyl amine were added dropwise. At −10° C. a solution of 25.0 ml (0.41 mol) of carbon disulfide in 100 ml of chloroform were added while stirring within 30 minutes and stirring was continued for one hour. Then, at 0° C., a solution of 40.0 ml (0.41 mol) of chloroformic acid ethyl ester in 70.0 ml of chloroform were added within 30 minutes and stirring was continued at room temperature for one hour. Then a solution of 57.0 ml (0.41 mol) of triethyl amine in 140 ml of chloroform were added during 15 minutes and stirring was continued for one hour. After addition of 420 ml of chloroform, a clear solution was obtained which was washed twice with a 5% sodium hydroxide solution and a 5% hydrochloric acid and water in each case. After drying with $Na_2SO_4$ the whole was evaporated and the crude isothiocyanate was immediately further reacted.

(b) 4-(3-Dimethylaminopropyl)-4-phenyl-3,4-dihydro-2H-isoquinolin-1thione 0.30 Mol of crude 2,2-diphenyl-5-dimethylaminopentyl-isothiocyanate was introduced within 30 minutes into 500 ml of concentrated sulfuric acid with stirring and cooling, whereby the reaction temperature should not exceed 40° C. Stirring was continued at room temperature for one hour. The reaction solution was subsequently poured as a thin jet onto 5.0 l of ice water and the alkaline aqueous phase was extracted with chloroform. The solution was dried with $Na_2SO_4$, evaporated and the residue was triturated with ethanol.

Melting point: 212° C. (oxalate).

(c) 4-(3-Dimethylaminopropyl)-4-phenyl-3,4-dihydro-2H-isoquinolin-1-thione 10 mmols of 2,2-diphenyl-5-dimethylamino-pentyl-isothiocyanate were added dropwise to a suspension of 15 mmols of aluminum chloride in 3.0 ml of carbon disulfide at room temperature and refluxed for 15 minutes. Then 10 ml of water were added dropwise while cooling and the mixture was made alkaline. The product was extracted with benzene, dried and the solvent was evaporated in vacuo. The amorphous resudue was triturated with ethyl acetate and the crystals suction-filtered.

Melting point: 210°–213° C. (oxalate).

(d) 4-(3-Dimethylaminopropyl)-4-phenyl-3,4-dihydro-2H-isoquinolin-1-thione 3.7 mmols of 2,2-diphenyl-5-dimethylaminopentyl-isothiocyanate and 7.5 mmols of aluminum chloride were triturated well and allowed to stand for 24 hours at room temperature. Then water was added carefully with cooling, the whole was extracted with benzene, dried and concentrated.

Melting point: 211° C. (oxalate).

(e) 4-(3-Dimethylaminopropyl)-4-phenyl-3,4-dihydro-2H-isoquinolin-1-one 4-(3-Dimethylaminopropyl-4-phenyl-3,4-dihydro-2H-isoquinolin-1-thione (0.02 mol) were refluxed for 4 hours with 50 ml of semi-concentrated hydrochloric acid. The mixture was taken up in chloroform and the organic phase was washed once with sodium bicarbonate and then with water, dried and concentrated.

Melting point: 157°–162° C. (oxalate).

(f) 4-(3-Dimethylaminopropyl)-4-phenyl-3,4-dihydro-2H-isoquinolin-1-one 0.02 mol of 4-(3-Dimethylaminopropyl)-4-phenyl-3,4-dihydro-2H-isoquinolin-1-thione was dissolved in 50 ml of ethanol and 1.1 g (0.01 mol) of selenium dioxide were added. The whole was refluxed for 4 hours, cooled, filtered from the undissolved material and concentrated.

Melting point: 159°–160° C. (oxalate).

EXAMPLE 2

4-(3-Dimethylamino-2-methyl-propyl)-4-phenyl-3,4-dihydro-2H-isoquinolin-1-one (a) 4-(3-dimethylamino-2-methyl-propyl)-4-phenyl-3,4-dihydro-2H-isoquinolin-1-thione From 2,2-diphenyl-4-methyl-5-dimethylamino-pentyl-amine in analogy to 1a and subsequent 1b.

Melting point: 215° C. (oxalate).

(b) 4-(3-Dimethylamino-2-methyl-propyl)-4-phenyl-3,4-dihydro-2H-isoquinolin-1-one From 4-(3-dimethylamino-2-methyl-propyl)-4-3,4-dihydro-2H-isoquinolin-1-thione in analogy to 1e.

Amorphous; NMR: γ:

—$CH_3$ singlet 2.4 (6 protons)
—$CH_3$ doublet 0.9 (3 protons)

EXAMPLE 3

4-(3-Piperidin-1-yl-propyl)-4-phenyl-3,4-dihydro-2H-isoquinolin-1-one (a) N-(2,2-diphenyl-5-piperidin-1-yl-n-pentyl)-carbamic acid ethyl ester 0.25 mol of 2,2-diphenyl-5-piperidino-1-yl-n-pentyl-aminohydrochloride was suspended in 650 ml of toluene and 71.6 g (0.68 mol) of anhydrous sodium carbonate. 46.4 g (0.43 mol) of chloroformic acid ethyl ester were added dropwise, while stirring, and the whole was refluxed for 5 hours. It was suction-filtered from the undissolved material and the filtrate was concentrated in vacuo. the urethane was further reacted in a crude state.

(b) 4-(3-Piperidin-1-yl-propyl)-4-phenyl-3,4-dihydro-2H-isoquinolin-1-one 0.2 mol of N-(2,2-diphenyl-5-piperidin-1-yl-n-pentyl)-carbamic acid ethyl ester was introduced into 500 ml of hot (130° C.) and stirred polyphosphoric acid so that the temperature was kept between 130° and 140° C. The temperature was kept for 10 minutes at 140° C. and, after cooling to 70°–80° C., the mixture was poured onto 2.0 l of ice water. After standing over night the water was decanted and the residue was extracted twice with water. The water phase was adjusted to an alkaline range, extracted with benzene, dried and concentrated in vacuo. The remaining oil was dissolved in about 40 ml of methanol and brought to crystallization by addition of seed crystals.

Melting point: 184°–185° C. (oxalate)

(c) 2,2-Diphenyl-5-piperidino-1-yl-n-pentyl-isocyanate 0.1 mol of 2,2-diphenyl-5-piperidin-1-yl-n-pentyl-amine hydrochloride was introduced into 200 ml of 1 m solution of phosgene in toluene and refluxed for 10 hours. After cooling, the mixture was extracted with water, adjusted to an alkaline range, extracted with $CHCl_3$, dried and evaporated. The isocyanate was further reacted in a crude state.

(d) 4-(3-Piperidin-1-yl-propyl)-4-phenyl-3,4-dihydro-2H-isoquinolin-1-one 20 mmols of crude 2,2-diphenyl-5-piperidino-1-yl-n-pentylisocyanate were added dropwise, while stirring, to a suspension of 2.9 g (22 mmols) of aluminum chloride in 20 ml of 1,2-dichloro-ethane and the temperature was kept below 30° C. Stirring was continued for one hour at room temperature and the mixture was carefully mixed with 30 ml of water and adjusted to an alkaline range. After addition of 20 ml of dichloroethane, the organic phase was separated, dried and concentrated. The residue was dissolved in 20 ml of methanol, filtered from the undissolved material and the solvent was evaporated. Crystals from a small amount of methanol were obtained.

Melting point: 183°–184° C. (oxalate).

(e) 4-(3-Piperidino-1-yl-propyl)-4-phenyl-3,4-dihydro-2H-isoquinolin-1-one 1.08 mols of N-(2,2-diphenyl-5-piperidiono-1-yl-n-pentyl)-carbamic acid ethyl ester were refluxed for 3 hours in 2.2 l of phoshorous oxychloride. The phoshorous oxychloride in excess was distilled in vacuo and the residue was poured onto ice water. The mixture was made alkaline with concentrated sodium hydroxide solution. The product was extracted with benzene, washed with water, dried and concentrated.

Melting point: 182°–184° C. (oxalate)

EXAMPLE 4

4-(2-Piperidino-1-yl-ethyl)-4-phenyl-3,4-dihydro-2H-isoquinolin-1-one (a) N-(2,2-diphenyl-4-piperidin-1-yl-butyl)-carbamic acid ethyl ester From 2,2-diphenyl-4-piperidino-1-yl-butyl amine in analogy to 3a.

Melting point: 95°–97° C.

(b) 4-(2-Piperidino-1yl-ethyl)-4-phenyl-3,4-dihydro-2H-isoquinolin-1-one

From N-(2,2-diphenyl-4-(piperidin-1-yl)-butyl)-carbamic acid ethyl ester in analogy to 3b.

Melting point: 98°–100° C.

EXAMPLE 5

4-(2-diisopropylamino-ethyl)-4-phenyl-3,4-dihydro-2H-isoquinolin-1-one (a) N-(2,2-diphenyl-4-diisopropylamino-butyl)-carbamic acid ethyl ester From 2,2-diphenyl-4-diisopropylamino-butyl-amine in analogy to 3a. The urethane was used in a crude state.

(b) 4-(2-diisopropylaminoethyl)-4-phenyl-3,4-dihydro-2H-isoquinolin-1-one

From N-(2,2-diphenyl-4-diisopropylamino-butyl)-carbamic acid ethyl ester in analogy to 3b.

EXAMPLE 6

4-(2-Pyrrolidino-1-yl-ethyl)-4-phenyl-3,4-dihydro-2H-isoquinolin-1-one (a) N-(2,2-diphenyl-4-pyrrolidin-1-yl-butyl)-carbamic acid ethyl ester From 2,2-diphenyl-4-pyrrolidin-1-yl-butyl amine in analogy to 3a. The urethane was further reacted in a crude state.

(b) 4-(2-Pyrrolidino-1-yl-ethyl)-4-phenyl-3,4-dihydro-2H-isoquinolin-1-one

From N-(2,2-diphenyl-4-pyrrolidino-1-yl-butyl)-carbamic acid ethyl ester in analogy to 3b.

Amorphous: NMR: γ:
CH$_2$ multiplet 2.2–2.6 (6 protons)
CH$_2$ multiplet 3.6–3.9 (2 protons)

EXAMPLE 7

4-(2-Dimethylaminoethyl)-4-phenyl-3.4-dihydro-2H-isoquinolin-1-one (a) N-(2,2-diphenyl-4-dimethylamino-butyl)-carbamic acid ethyl ester From 2,2-diphenyl-4-dimethylamine-butylamine in analogy to 3a. The urethane was further reacted in a crude state.

(b) 4-(2-Dimethylaminoethyl)-4-phenyl-3,4-dihydro-2H-isoquinolin-1-one

From N-(2,2-diphenyl-4-dimethylamino-butyl)-carbamic acid ethyl ester in analogy to 3b.

Melting point: 183° C. (oxalate).

EXAMPLE 8

4-(2-Di-n-butylaminoethyl)-4-phenyl-3,4-dihydro-2H-isoquinolin-1-one (a) N-(2,2-diphenyl-4-di-n-butylamino-butyl)-carbamic acid ethyl ester From 2,2-diphenyl-4-di-n-butylaminobutyl-amine in analogy to 3a. The crude urethane was further reacted in a crude state.

(b) 4-(3-Di-n-butylaminoethyl)-4-phenyl-3,4-dihydro-2H-isoquinolin-1-one

From N-(2,2-diphenyl-4-di-n-butylamino-butyl)-carbamic acid ethyl ester in analogy to 3b.

Melting point: 165° C. (oxalate).

EXAMPLE 9

4-(2-Diethylaminoethyl)-4-phenyl-3,4-dihydro-2H-isoquinolin-1-one (a) N-(2,2-Diphenyl-4-diethylaminobutyl)-carbamic acid ethyl ester From 2,2-diphenyl-4-diethylaminobutylamine in analogy to 3a.

The urethane was further reacted in a crude state.

(b) 4-(2-Diethylaminoethyl)-4-phenyl-3,4-dihydro-2H-isoquinolin-1-one

From N-(2,2-diphenyl-4-diethylaminobutyl)-carbamic acid ethyl ester in analogy to 3b.

Melting point: 176° C.

EXAMPLE 10

4-(2-Diethylaminoethyl)-4-methyl-3,4-dihydro-2H-isoquinolin-1-one (a) N-(2-Methyl-2-phenyl-4-diethylamino-butyl)-carbamic acid ethyl ester From 2-methyl-2-phenyl-4-diethylaminobutylamine in analogy to 3a.

Boiling point: 190° C./1 mm Hg.

(b) 4-(2-Diethylaminoethyl)-4-methyl-3,4-dihydro-2H-isoquinolin-1-one

From N-(2-methyl-2-phenyl-4-diethylaminobutyl)-carbamic acid ethyl ester.

Melting point: 174°–177° C. (oxalate)

EXAMPLE 11

4-(2-Diethylaminoethyl)-4-ethyl-3,4-dihydro-2H-isoquinolin-1-one (a) N-(2-Ethyl-2-phenyl-4-diethylaminobutyl)-carbamic acid ethyl ester From 2-ethyl-2-phenyl-4-diethylamino-butylamine in analogy to 3a. The urethane was further reacted in a pure state.

(b) 4-(2-Diethylaminoethyl)-4-ethyl-3,4-dihydro-2H-isoquinolin-1-one

From N-(2-ethyl-2-phenyl-4-diethylamino-butyl)-carbamic acid ethyl ester is analogy to 3b.

Melting point: 125°–130° C. (oxalate).

EXAMPLE 12

4-(2-diisopropylaminoethyl)-4-phenyl-6-methoxy-3,4-dihydro-2H-isoquinolin-1-one (a) N-(2-Phenyl-2(3-methoxyphenyl)-4-diethylaminobutyl)-carbamic acid ethyl ester From 2-phenyl-2-(3-methoxyphenyl)-4-diethylaminobutylamine in analogy to 3a.

The urethane was further reacted in a crude state.

(b) 4-(2-Diisopropylaminoethyl)-4-phenyl-6-methoxy-3,4-dihydro-2H-isoquinolin-1-one From N-(2-phenyl-2-(3-methoxyphenyl)-4-diethylamino-butyl)carbamic acid ethyl ester in analogy to 3e.

Melting point: 133°–135° C. (Hydrochloride)

EXAMPLE 13

4-(2-Diethylaminoethyl)-6,7-dimethyoxy-3,4-dihydro-2H-isoquinolin-1-one (a) N-(2-(3,4-dimethoxyphenyl)-4-diethylaminobutyl)-carbamic acid ethyl ester From 2-(3,4-dimethoxyphenyl)-4-diethylaminobutylamine in analogy to 3a. The urethane was further reacted in a crude state.

(b) 4-(2-Diethylaminoethyl)-6,7-dimethoxy-3,4-dihydro-2H-isoquinolin-1-one

From N-(2-(3,4-dimethoxyphenyl)-4-diethylaminobutyl)-carbamic acid ethyl ester in analogy to 3e.

Melting point: 197° C. (hydrochloride).

The starting compounds of the formula XV and XIV for the preparation as described in Examples 1 to 13 of the compounds of the invention of the formula I are listed in the following Tables 1 and 2, respectively.

TABLE 1

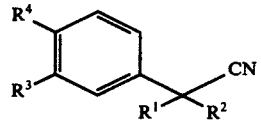

XV

| R$^1$ | R$^2$ | R$^3$ | R$^4$ | Method | boiling point/ melting point (mp) (bp) in ° C |
|---|---|---|---|---|---|
| 1) C$_6$H$_5$ | —(CH$_2$)$_3$—N(CH$_3$)$_2$ | H | H | A | mp :66° C |
| 2) C$_6$H$_5$ | —CH$_2$—CH(CH$_3$)—CH$_2$—N(CH$_3$)$_2$ | H | H | A | mp :55° C |
| 3) C$_6$H$_5$ | —(CH$_2$)$_3$—N(piperidine) | H | H | A | Crude product |
| 4) C$_6$H$_5$ | —(CH$_2$)$_2$—N(piperidine) | H | H | A | mp :74–76° C |
| 5) C$_6$H$_5$ | —(CH$_2$)$_2$—N(i-C$_3$H$_7$)$_2$ | H | H | A | bp: 175–182° C/ 0.3 mmHg |
| 6) C$_6$H$_5$ | —(CH$_2$)$_2$—N(pyrrolidine) | H | H | A | bp: 165–168° C/ 0.3 mmHg |
| 7) C$_6$H$_5$ | —(CH$_2$)$_2$—N(CH$_3$)$_2$ | H | H | A | bp: 152° C/ 0.7 mmHg |
| 8) C$_6$H$_5$ | —(CH$_2$)$_2$—N(n-C$_4$H$_9$)$_2$ | H | H | A | bp: 185–186° C/ 0.7 mmHg |
| 9) C$_6$H$_5$ | —(CH$_2$)$_2$—N(C$_2$H$_5$)$_2$ | H | H | A | bp: 155–165° C/ 0.5 mmHg |
| 10) CH$_3$ | —(CH$_2$)$_2$—N(C$_2$H$_5$)$_2$ | H | H | A | bp: 116–122° C/ 0.6 mmHg |
| 11) C$_2$H$_5$ | —(CH$_2$)$_2$—N(C$_2$H$_5$)$_2$ | H | H | A | bp: 126–128° C/ 0.7 mmHg |
| 12) C$_6$H$_5$ | —(CH$_2$)$_2$—N(i-C$_3$H$_7$)$_2$ | OCH$_3$ | H | B | bp: 180–185° C/ 0.5 mmHg |
| 13) H | —(CH$_2$)$_2$—N(C$_2$H$_5$)$_2$ | OCH$_3$ | OCH$_3$ | A | bp: 175–179° C/ 0.6 mmHg |

TABLE 2:

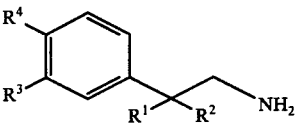

XIV

| R¹ | R² | R³ | R⁴ | mp (in ° C) / δ (NMR) in ppm | |
|---|---|---|---|---|---|
| 1) $C_6H_5$ | $-(CH_2)_3-N(CH_3)_2$ | H | H | $CH_3$:s<br>$NH_2$:s | crude product<br>2.05 (6 protons)<br>1.4 (2 protons) |
| 2) $C_6H_5$ | $-CH_2-CH(CH_3)-CH_2-N(CH_3)_2$ | H | H | $CH_3$:s<br>$CH_3$:d | crude product<br>2.1 (6 protons)<br>1.6 (3 protons) |
| 3) $C_6H_5$ | $-(CH_2)_3-N\diagup\diagdown$ (piperidine) | H | H | $C_6H_5$:m<br>Aliphat.:m | crude product<br>7.2-7.6 (10 protons)<br>0.95-3.15 (18 protons) |
| 4) $C_6H_5$ | $-(CH_2)_2-N\diagup\diagdown$ (piperidine) | H | H | | mp: 93-94° C |
| 5) $C_6H_5$ | $-(CH_2)_2-N(i-C_3H_7)_2$ | H | H | | mp: 58° C |
| 6) $C_6H_5$ | $-(CH_2)_2-N\diagup\diagdown$ (pyrrolidine) | H | H | $C_6H_5$:m<br>Aliphat.:m | crude product<br>7.15-7.75 (10 protons)<br>1.15-2.97 (14 protons) |
| 7) $C_6H_5$ | $-(CH_2)_2-N(CH_3)_2$ | H | H | $CH_3$:s | crude product<br>1.95 (6 protons) |
| 8) $C_6H_5$ | $-(CH_2)_2-N(n-C_4H_9)_2$ | H | H | $CH_3$:t | crude product<br>1.12 (6 protons) |
| 9) $C_6H_5$ | $-(CH_2)_2-N(C_2H_5)_2$ | H | H | $CH_3$:t | crude product<br>1.1 |
| 10) $CH_3$ | $-(CH_2)_2-N(C_2H_5)_2$ | H | H | $CH_3$:t<br>$CH_3$:s | crude product<br>1.05 (6 protons)<br>1.4 (3 protons) |
| 11) $C_2H_5$ | $-(CH_2)_2-N(C_2H_5)_2$ | H | H | $CH_3$:m | crude product<br>0.8-1.4 (9 protons) |
| 12) $C_6H_5$ | $-(CH_2)_2-N(i-C_3H_7)_2$ | $OCH_3$ | H | $CH_3$:d<br>$OCH_3$:s | crude product<br>1.3 (12 protons)<br>3.8 (3 protons) |
| 13) H | $-(CH_2)_2-N(C_2H_5)_2$ | $OCH_3$ | $OCH_3$ | CH :m<br>$OCH_3$:s | 4.05 (1 protons)<br>3.9 (6 protons) |

What we claim is:

1. A 3,4-dihydroisoquinoline of the formula

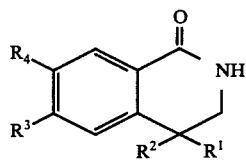

or a pharmaceutically acceptable salt thereof, wherein
$R^1$ is methyl, ethyl, or phenyl;
$R^2$ is

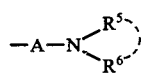

wherein A is straight-chain or branched alkylene having 2 or 3 carbon atoms and $R^5$ and $R^6$ are the same alkyl having 1 to 4 carbon atoms; and
$R^3$ and $R^4$ are the same or different and are hydrogen or lower alkoxy having 1 to 4 carbon atoms.

2. A compound as claimed in claim 1 which is 4-(2-diisopropylaminoethyl)-4-phenyl-3,4-dihydro-2H-isoquinolin-1-one.

3. A compound as claimed in claim 1 which is 4-(2-diethylaminoethyl)-6,7-dimethoxy-3,4-dihydro-2H-isoquinolin-1-one.

4. A pharmaceutical composition for treating arrhythmia which comprises a pharmaceutical carrier and an anti-arrhythmically effective amount of a compound as claimed in claim 1.

5. The method of treating disturbances of the cardiac rhythm in a patient suffering therefrom which comprises internally administering to said patient a therapeutically effective amount of a compound as claimed in claim 1.